United States Patent
Jensen et al.

(10) Patent No.: US 6,228,044 B1
(45) Date of Patent: *May 8, 2001

(54) METHODS AND APPARATUS FOR TREATING PLANTAR ULCERATIONS

(75) Inventors: Jeffrey L. Jensen, Highlands Ranch; Paul P. Burek, Aurora, both of CO (US)

(73) Assignee: Rose Biomedical Research, Denver, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/225,822

(22) Filed: Jan. 5, 1999

(51) Int. Cl.$^7$ ............................................. A61F 5/00
(52) U.S. Cl. .................................. 602/27; 602/23
(58) Field of Search ................. 602/27, 13, 20, 602/60, 23; 128/847, 892, 882, DIG. 20; 5/648, 650, 651; 601/27, 33

(56) References Cited

U.S. PATENT DOCUMENTS

| Re. 34,661 | 7/1994 | Grim . |
|---|---|---|
| 3,083,708 | 4/1963 | Gottfried . |
| 3,338,237 | 8/1967 | Sconce . |
| 3,351,055 | 11/1967 | Gottfield . |
| 3,580,248 | 5/1971 | Larson . |
| 3,701,349 | 10/1972 | Larson . |
| 3,760,056 | 9/1973 | Rudy . |
| 3,811,434 | 5/1974 | Jacobson et al. . |
| 3,955,565 | * 5/1976 | Johnson, Jr. ............... 128/89 |
| 4,076,022 | 2/1978 | Walker . |
| 4,320,748 | 3/1982 | Racette et al. . |
| 4,454,871 | 6/1984 | Mann et al. . |

(List continued on next page.)

FOREIGN PATENT DOCUMENTS

| 470174 | 5/1969 | (CH) . |
|---|---|---|
| 440113 | 1/1927 | (DE) . |
| 837750 | 5/1952 | (DE) . |
| 867585 | 1/1953 | (DE) . |
| 1171361 | 11/1969 | (GB) . |

OTHER PUBLICATIONS

Tuffley et al., "Pneumatic Bandage for Use . . .", The Lancet, Feb. 22, 1964, pp. 415, 416.

(List continued on next page.)

*Primary Examiner*—Mickey Yu
*Assistant Examiner*—Denise Pothier
(74) *Attorney, Agent, or Firm*—Gibson, Dunn & Crutcher LLP

(57) ABSTRACT

The present invention provides methods and an apparatus for treating patients having ulcerations of the lower foot, including patients suffering from diabetic neuropathy. The brace generally includes a pair of rigid shells, a fastening system for joining the shells together to form a unified brace and a combination of bladders which engage the patient's leg and ankle to off-weight the plantar surface, prevent plantar flexing and minimize shearing forces to the plantar surface. The volume of the bladders may be adjusted by the addition or removal of a filler in order to maintain a uniform pressure between the bladders and the patient's leg. The filler contained in the bladders preferably does not undergo significant expansion or contraction in response to temperature or altitude changes. The brace also preferably includes a series of full-length bladders and a specially designed adjustable bladder located within the ankle and heel region of the brace to maximize off-weighting and to prevent the foot from moving downward toward the footbed of the brace. In addition to providing an effective means for off-weighting the plantar surface of a patient, the brace is reuseable, easy to apply and fully adjustable to accommodate changes in a patient's leg size.

15 Claims, 10 Drawing Sheets

U.S. PATENT DOCUMENTS

| | | |
|---|---|---|
| 4,502,470 | 3/1985 | Kiser et al. . |
| 4,641,639 | 2/1987 | Padilla . |
| 4,693,239 | 9/1987 | Clover, Jr. . |
| 4,805,601 | 2/1989 | Eischen, Sr. . |
| 4,844,094 | 7/1989 | Grim . |
| 4,869,267 | 9/1989 | Grim et al. . |
| 4,913,755 | 4/1990 | Grim . |
| 4,964,402 | 10/1990 | Grim et al. . |
| 4,996,979 | 3/1991 | Grim et al. . |
| 5,027,801 | 7/1991 | Grim . |
| 5,078,128 | 1/1992 | Grim et al. . |
| 5,125,400 | 6/1992 | Johnson, Jr. . |
| 5,139,475 | 8/1992 | Robicsek . |
| 5,197,942 * | 3/1993 | Brady .......................... 602/5 |
| 5,218,954 | 6/1993 | van Bemmelen . |
| 5,226,245 | 7/1993 | Lamont . |
| 5,277,695 | 1/1994 | Johnson, Jr. et al. . |
| 5,329,705 | 7/1994 | Grim et al. . |
| 5,348,530 | 9/1994 | Grim et al. . |
| 5,354,260 | 10/1994 | Cook . |
| 5,370,133 | 12/1994 | Darby et al. . |
| 5,389,065 | 2/1995 | Johnson, Jr. . |
| 5,399,152 | 3/1995 | Habermeyer et al. . |
| 5,403,265 | 4/1995 | Berguer et al. . |
| 5,419,757 | 5/1995 | Daneshvar . |
| 5,435,009 | 7/1995 | Schild et al. . |
| 5,453,082 | 9/1995 | Lamont . |
| 5,464,385 | 11/1995 | Grim . |
| 5,466,250 | 11/1995 | Johnson, Jr. et al. . |
| 5,503,622 | 4/1996 | Wehr . |
| 5,520,628 | 5/1996 | Wehr . |
| 5,527,269 * | 6/1996 | Reithofer .......................... 602/27 |
| 5,571,077 | 11/1996 | Klearman et al. . |
| 5,577,998 | 11/1996 | Johnson, Jr. et al. . |
| 5,605,535 | 2/1997 | Lepage . |
| 5,609,570 | 3/1997 | Lamont . |
| 5,620,411 | 4/1997 | Schumann et al. . |
| 5,665,059 | 9/1997 | Klearman et al. . |
| 5,761,834 | 6/1998 | Grim et al. . |
| 5,778,565 | 7/1998 | Holt et al. . |
| 5,792,084 * | 8/1998 | Wilson et al. .......................... 602/13 |
| 5,833,639 * | 11/1998 | Nunes et al. . |
| 5,839,139 * | 11/1998 | Fink .......................... 5/648 |

OTHER PUBLICATIONS

Ulbrecht et al., "Controversies in Footwear . . .", pp. 441–451.

Fleischli et al., "Comparison of Strategies for Reducing . . .", Journal of the American Podiatric Medical Association, vol. 87, No. 10, Oct. 1997, 466–472.

Scholl, William M. PhD., "Scholl Human Orthopedics and Engineering Labs", Version 1.2.

Shaw et al., "The Mechansim of Plantar Unloading in . . .", Foot & Ankle International, vol. 18, No. 12, Dec. 1997, pp. 809–817.

Armstrong et al., "Peak Foot Pressures Influence the . . .", Journal of rehabilitation Research and Development., vol. 35, No. 1, Jan. 1998, pp. 1–5.

Baumhauer et al., "A Comparison Study of Plantar Foot . . . ", Foot & Ankle International, vol. 18, No. 1, Jan. 1997, pp. 26–33.

Aircast, Inc., "Pneumatic Walker Diabetic System", Brochure produced by Aircast, Inc.

* cited by examiner

METHODS AND APPARATUS FOR TREATING PLANTAR ULCERATIONS

FIELD OF THE INVENTION

The present invention relates to the field of foot treatment and more particularly to the field of treating ulcers on the plantar surface of the foot. The present invention also relates to the field of leg braces. Unlike other devices for treating plantar ulcers, the brace of the present invention is reuseable, adjustable to a variety of leg sizes, easily applied and capable, through the use of a novel system of bladders and other design features, of effectively off-weighting the plantar surface and reducing shearing forces thereto, thereby allowing the ulcers to heal.

BACKGROUND

The development of effective means for treating foot sores or ulcerations, especially diabetic foot ulcerations, presents a significant medical challenge. Diabetic foot ulcers result in more than 55,000 lower extremity amputations per year (nearly half of all amputations performed in the United States) and account for more hospitalizations than any other single complication of diabetes. Of the 14 million diagnosed diabetics, 15 percent, or 2.1 million, suffer from foot ulcerations. In fact, foot ulcers are the leading cause of hospitalization of patients with diabetes and account for 10 percent of the costs related to diabetic care.

The burdens of such complications can also have a devastating effect on patients and their families. Patients' quality of life can rapidly decline leaving them unable to work, and dependent on family members to spend their time and resources caring for the patient. Disabilities due to diabetes result in more than $5.6 billion per year in lost wages and earnings.

The problem is compounded by the fact that many diabetics suffer from peripheral neuropathy and thus cannot feel pain. Since pain is often a primary incentive for patient compliance, neuropathy patients frequently do not comply with voluntary off-weighting techniques, resulting in further deterioration of the wound and possibly leading to infection. It is, therefore, crucial that the off-weighting treatment device does not set patients up for failure by allowing them to walk on the wound, thus preventing healing.

The typical cycle for this medical complication is chronic foot ulceration, infection, hospitalization, amputation and rehabilitation. This costly cascade of events need not take place since two-thirds of diabetic amputees do have an adequate blood supply to heal ulcerations. The key factor for effective treatment then is to remove the patient's weight from the ulcerated site to give the ulcers an opportunity to heal.

Currently, there are several options for off-weighting diabetic foot ulcers to enable them to heal. These options have varying degrees of success depending upon the degree of patient compliance, wound location, and grade of wound. The following is a brief description of the most frequently used therapies for treating diabetic foot ulcers and their advantages and disadvantages.

Prescribing the use of crutches and/or wheelchair use is perhaps one of the simpler treatment methods. However, these options have produced poor clinical results due to lack of patient compliance. Patients with peripheral neuropathy in particular are not motivated to use these devices.

A variety of specially designed sandals and modified shoes have been tried. One sandal, referred to as the temporary healing sandal, provides a cut-out region in the sole to alleviate pressure to the ulcerated site. The problem with this type of sandal is that since the human foot is not flat, when pressure is removed from the area of the ulcer site, there is increased pressure to other metatarsal heads which creates the potential for transfer lesions. A second sandal, the custom sandal, is made from an impression of the patient's foot. Like the temporary sandal, an area in the sole aligned with the location of the ulcers is cut out to relieve pressure at the ulcerated site. Because the patient's weight is more evenly distributed as compared to the temporary healing sandal, the likelihood of transfer lesions being formed is reduced. However, this type of sandal provides no relief from shearing forces.

Several devices generically referred to as "walkers" have been designed which are similar to the sandals just described. The DH Walker, for example, is similar in design to the temporary healing sandal. It includes a flat surface upon which the foot rests, but the surface includes plugs which can be removed to accommodate the area of the wound. Not surprisingly given the similarity in design, the DH Walker suffers from the same problem as the temporary sandal in that weight is transferred to adjacent metatarsal heads and the potential for the formation of transfer lesions is great. The sandal also fails to alleviate shearing forces. Another walker called the Cam Walker is essentially equivalent to a DH walker, except that it does not have removable plugs within the device. Consequently, the Cam Walker does not effectively off-weight the wound.

A variety of modified shoes have been tried. Ipos shoes are half shoes that are cut off at the middle of the foot, leaving the forefoot overhanging the cut-off area. Studies have shown that this shoe can be effective, provided the patient is diligent in wearing it. Compliance during the evening, however, is often a problem. Moreover, the Ipos shoe is only applicable to forefoot ulcers and has a high potential for generating transfer lesions.

A different approach involves placing felt directly on the foot and then covering the felt with foam which includes a cut-out region to correspond to the location of the wound. This approach has been shown to be efficacious. However, the method can also cause damage to the skin during the removal process, since the plantar skin can be easily torn.

The Charcot Restraint Orthotic Walker (C.R.O.W.) is a cast manufactured of polypropylene which is effective in the treatment of plantar ulcerations, but only so long as the leg remains the size it was when first casted. Cost is another problem; the average casting cost is $1,200 per cast. In general, C.R.O.W.s have shown limited utility since changes in the patients' leg reduce the effectiveness at which the foot is off-weighted over time.

All of these methods have proven successful provided they are used on the right patient at the right time, and that patient compliance is not an issue. However, the primary current ambulatory method that ensures off-weighting of the wound is the Total Contact Cast (TCC). The TCC is a cast that is formed using a complicated procedure involving wrapping the patient's leg in plaster wrap and fiberglass. Although the TCC has the disadvantage of being difficult to apply, it has been shown to be effective in healing up to 90 percent of cases.

Total contact casts relieve the forces that prevent healing by: 1) shortening stride length, 2) decreasing walking velocity (which diminishes vertical forces), 3) eliminating motion at the ankle joint (sagittal plane), 4) eliminating the propulsive phase of gait, 5) redirecting body weight from the foot to the lower leg, and 6) eliminating shearing forces. One study concluded that the effectiveness of the TCC is a consequence of its ability to decrease plantar pressures to nearly imperceptible levels (as low as 0.34 N/cm$^2$) and to essentially eliminate motion in the cast, thus substantially curtailing shearing forces (Todd, W. F., et al. Wound/Ostomy Management, 41: 48–49, 1995).

Yet, despite its efficacy when used properly, numerous difficulties have resulted in significantly lower TCC usage than might be expected. First, application of the total contact cast is a complex, 15-step process requiring a high degree of skill and approximately one hour of time to complete. Improper application can also have significant negative consequences. For example, casts applied over an active infection raise the potential for loss of the infected leg, improper application of the cast can create new ulcerations, and the failure to remove wrinkles in the stocking inside the cast may irritate the patient's skin.

Secondly, the TCC cannot accommodate the changes in patient leg size which frequently occur due to decreased edema and atrophy of the muscle. Typically, the patient must be re-examined three days after the initial casting to check for decreases in leg volume that could allow the leg to "piston" (slide) within the cast. Pistoning requires immediate recasting. Casts that consistently piston call for weekly recasting. Even casts that do not piston must still be changed at least every two weeks. Patients with large wounds may require recasting twice per week. Patients must be vigilant for abnormalities which require an immediate cast change. Thus, the complexity of the casting process is compounded by the frequent need for a recasting and the high cost of multiple applications.

Finally, cast removal is also difficult, and improper removal can have adverse consequences. For example, because there is little or no interior padding in the TCC, utilizing a saw to remove the cast without cutting, abrading or burning the patient requires significant practice. Incorrect technique can result in lacerations to the patient's leg.

For the foregoing reasons, many physicians have opted to use other methods for treating plantar ulcers. Moreover, even if physicians could be properly trained on a widespread scale to apply and remove the TCC, it is doubtful that use of the TCC would increase significantly since many practitioners find that such time-consuming and labor intensive procedures are not profitable.

While the TCC and the other devices listed above have been specifically designed to address the need to treat patients suffering plantar ulcers, it should also be noted that a number of related adjustable leg casts have also been developed. These casts have significant advantages since they are adjustable and reuseable. These casts, however, differ from the TCC and the brace of the present invention in that the casts are designed primarily for fracture care rather than for treating plantar ulcers.

One example of such a cast is described in U.S. Pat. Nos. 3,580,248 and 3,701,349 to Larson. The cast includes two rigid, plastic shells, each containing an inflatable air bag disposed therein. These air bags run essentially the full length of the cast and filly surround the leg. Once a patient's leg is inserted into cast and the two halves fastened together, air can be used to inflate the bags to create a pressure against the leg for immobilizing the fractured limb.

A second example of such a cast includes the one described in U.S. Pat. No. 3,995,565 to Johnson, Jr. This cast is quite similar in construction to that described in the Larson patents and is also designed to treat fractures. However, the shells in the Johnson cast have sufficient flexibility so that the edges of one shell can be flexed to fit over the edges of the other shell. This enables the two shells to be radially adjusted with respect to each other to increase and decrease the size of the cast interior, thereby allowing the cast to accommodate a variety of leg sizes. Like the Larson cast, the Johnson cast includes air bags in both shell halves. Unlike the Larson cast, inflated air bags need not fully surround the leg; rather there are sections in which the shell and a portion of the leg are in indirect abutting relationship, the shell and leg only being separated by an uninflated portion of the air bag.

Because these casts are designed primarily for fracture care, they function quite differently than the brace of the current invention. As casts, these devices are designed primarily to immobilize an area surrounding the fracture; in particular, the casts are designed primarily to prevent flexing of the fracture. The device of the current invention, however, is not a cast but a brace. It is designed not to simply prevent a bone from flexing, but acts to redirect or redistribute a patient's weight throughout the brace itself rather than the patients foot More specifically, the brace of the present invention accomplishes the more difficult goals of effectively off-weighting the plantar surface of a patients foot, immobilizing the patient's ankle to prevent plantar flexing and significantly reducing shearing forces at the plantar surface. Existing casts do not appear to effectively achieve all of these results.

Thus, in view of the limitations of the current devices specifically designed for treating plantar ulcers, as well as casts designed for fracture care, there is a need for a device which is equally effective as the TCC in treating patients suffering from plantar ulcerations but without its associated limitations. In particular, there is a need for a brace which off-weights the plantar surface and prevents flexing of the foot within the brace in order to minimize the shearing forces on the ulcerated sites and promote rapid healing. Unlike the TCC, however, the brace should be easily applied and removed, reuseable and adjustable.

SUMMARY OF INVENTION

The brace of the present invention satisfies the need identified above. Unlike current adjustable casts which only restrict the fractured limb from flexing, the brace of the current invention satisfies the key requirements for effective treatment of plantar ulcerations: 1) the brace off-weights the plantar surface, i.e., the brace redistributes a patient's weight throughout the brace so that there is little or no direct pressure of the plantar surface against the footbed of the brace, 2) the brace restricts downward movement of the foot toward the footbed about the ankle joint, i.e., the brace restricts plantar flexing and 3) the brace significantly reduces shearing forces at the plantar surface. To achieve these goals, the brace of the present invention involves a novel design including a complementary pair of rigid shells and a unique combination of adjustable bladders, as well as cushions which need not be adjustable. Unlike existing casts, the brace of the current invention includes a combination of full-length and ankle bladders to effectively immobilize the leg within the cast and to prevent plantar flexing about the ankle joint. Furthermore, whereas other adjustable casts use air to inflate the bladders, the brace of the current invention preferably utilizes special fillers which have a thermal coefficient of expansion which is less than that of air. This ensures that there is consistent pressure against the leg and avoids the discomfort and the potential of the leg pistoning within the brace which can occur when air within the bladders expands or contracts with changes in temperature or altitude.

The brace of the present invention includes a number of additional benefits and avoids the inherent problems associated with the application and removal of the TCC. For example, the brace of the present invention ensures consistency of care between specialists (vascular surgeons, plastic surgeons, orthopedic surgeons, podiatrists, physical therapists and ET nurses) because only minimal practitioner intervention is required during the treatment period. Further, the brace is removable, easily modified to conform to changes in leg size as swelling decreases, restricts motion at the ankle joint, eliminates the propulsive phase of gait and shearing forces, and is easily applied and removed from the patient. Because the brace is highly effective in off-weighting the plantar surface, the brace is especially useful in treating the plantar ulcers of neuropathy patients that are incapable of recognizing and communicating physical discomfort in the foot and leg.

The brace of the present invention generally comprises: (a) a pair of rigid shells which are adapted to receive the lower portion of a patient's leg, (b) a fastening system which joins the first and second shell and immobilizes the shells around the patient's leg, (c) and at least one adjustable bladder disposed within the first or second shell which is capable of engaging the brace against the patient's leg such that the patient's leg does not move within the brace and the plantar surface is off-weighted. The brace also significantly reduces plantar flexing and shearing forces at the plantar surface.

More specifically, the shells of the brace include a first and second shell which are generally L-shaped. These shells have a generally semi-cylindrical cross-sectional configuration and are adapted for receiving a lower leg and a foot of a patient suffering from plantar ulcerations. Both shells including a vertical and horizontal section. The vertical section of the first shell has sufficient length to extend from a the patient's calf to a location beneath the heel portion of the patient's foot. Hence, the vertical section of the first shell includes a calf section and an ankle section which are adapted to receive the patient's calf and ankle, respectively. The horizontal section of the first shell extends outwardly at substantially a right angle to the vertical section of the first shell and has sufficient length to receive at least a majority of the patient's foot and preferably extends the length of the patient's foot. In like manner, the vertical section of the second shell has sufficient longitudinal dimension to extend from the patient's shin to the instep. The horizontal section of the second shell extends outwardly from the vertical section of the second shell at substantially a right angle and has sufficient length to cover at least a majority of the top of the patient's foot and preferably covers the entire length of the top of the patient's foot.

The brace also preferably includes a first adjustable bladder positioned in the first shell and a second bladder or cushion which is positioned in the second shell. At least the first bladder is adjustable, i.e., filler material can be injected or withdrawn in order to maintain a relatively constant desired pressure of the brace bladder against the leg. The ability to adjust the interior volume of the brace using the adjustable bladder(s) allows the brace to accommodate a variety of leg sizes and means the size of the bladders can be altered in accordance with changes in altitude or with changes in the patient's leg size resulting from edema or atrophy. These bladders preferably contain a filler which undergoes only minimal expansion or contraction with changes in altitude or with temperature changes within the brace which arise due to fluctuations in ambient temperature and/or changes in patient activity. The filler should have a lower thermal coefficient of expansion than air. Especially preferred fillers include those which are substantially non-compressible such as non-compressible silicone. Other potential fillers include injectible polyurethane foam, silicone wax liquid composites and compressible silicone liquid. Although it is used nearly exclusively in existing inflatable casts, air is not a preferred filler given its tendency to expand and contract with changes in temperature and altitude.

In a preferred embodiment, the brace also includes a third bladder. The volume of this bladder is preferably adjustable and the third bladder is positioned in the ankle region of the first shell. The third bladder also preferably has a structure in which two wings are located on opposing sides of a central region which is connected to the interior of the first shell. These wings can be wrapped around the patient's ankle region, including the sides of the patient's ankle. The third bladder is important in effectively immobilizing the patient's ankle and preventing plantar flexing.

A fastening system attached to the shells immobilizes the first and second shell around the patient's leg to form a unified brace. The fastening system can include a variety of systems but typically includes some type of strap which is anchored to one side of the first shell, passes over the second shell and is connected to the other side of the first shell. Thus, belts made of hook and loop type material (e.g., material sold under the trademark VELCRO) can be used. Various buckle systems can also be employed, including systems comprising serrated straps which connect to a cam mechanism. A locking mechanism can be added to prevent patients or other unauthorized personnel from opening the brace before the treatment program has been completed.

A layer of absorbent material can optionally be attached to the bladders to form a layer between the inserted leg and the bladders. This absorbent layer wicks away moisture from the patient to increase overall comfort and to minimize allergic reactions for patients with sensitive skin.

A cushion is attached to the footbed of the first shell. The cushion is made of materials which mold to the bottom of the foot such as low density foam or silicone. Although there is only minimal pressure on the bottom of a patient's foot, the cushion is designed to enhance the patient's comfort and to minimize shearing forces and friction.

A pressure sensor or transducer can be positioned between a bladder and the interior surface of the shell to enable clinicians to easily and accurately monitor the pressure of the bladders against the patient's leg. Proper pressure levels are important to ensure that there is adequate pressure to prevent movement of the leg within the brace; yet, the pressure cannot be unduly excessive such that blood circulation through the leg is compromised. Pressure can also be monitored by measuring back pressure at the inlet valve for the bladder and then using a previously determined relationship between back pressure at the valve to pressures on the leg to calculate leg pressure.

The present invention also includes a method for treating patients suffering from ulcerations on the plantar surface utilizing the brace of the present invention. The method generally comprises: (a) inserting a patient's leg between a set of first and second shells which are adapted to receive the lower leg and foot of a patient, (b) positioning at least one adjustable bladder so that it is sandwiched between the first or second shell and the patient's leg, (c) fastening the shells together using a fastening system to form a unified brace; and (d) adjusting the volume of the adjustable bladder(s) to engage the brace against the patient's leg so that the patient's leg does not move within the brace and the patient's plantar surface is off-weighted.

More specifically, the method preferably includes placing the patient's leg within the first shell and arranging the first bladder (and third bladder, if present) to surround the calf and ankle region of the leg. Care is taken to avoid direct contact between the ulcerated portion of the foot and the footbed of the first shell. The second shell is placed over the front of the patient's leg and the bladder disposed within the second shell arranged to cover the shin and instep portion of the patient's leg. The two shells are then fastened together using the fastening system to form a unified brace around the patient's leg. Filler material is then added into the adjustable bladders to create a desired uniform pressure around the circumference of the leg. This uniform pressure redistributes the patient's weight throughout the brace and off-weights the plantar surface. The pressure also immobilizes the ankle to prevent plantar flexing.

DETAILED DESCRIPTION OF PREFERRED EMBODIMENTS

Figure 1:
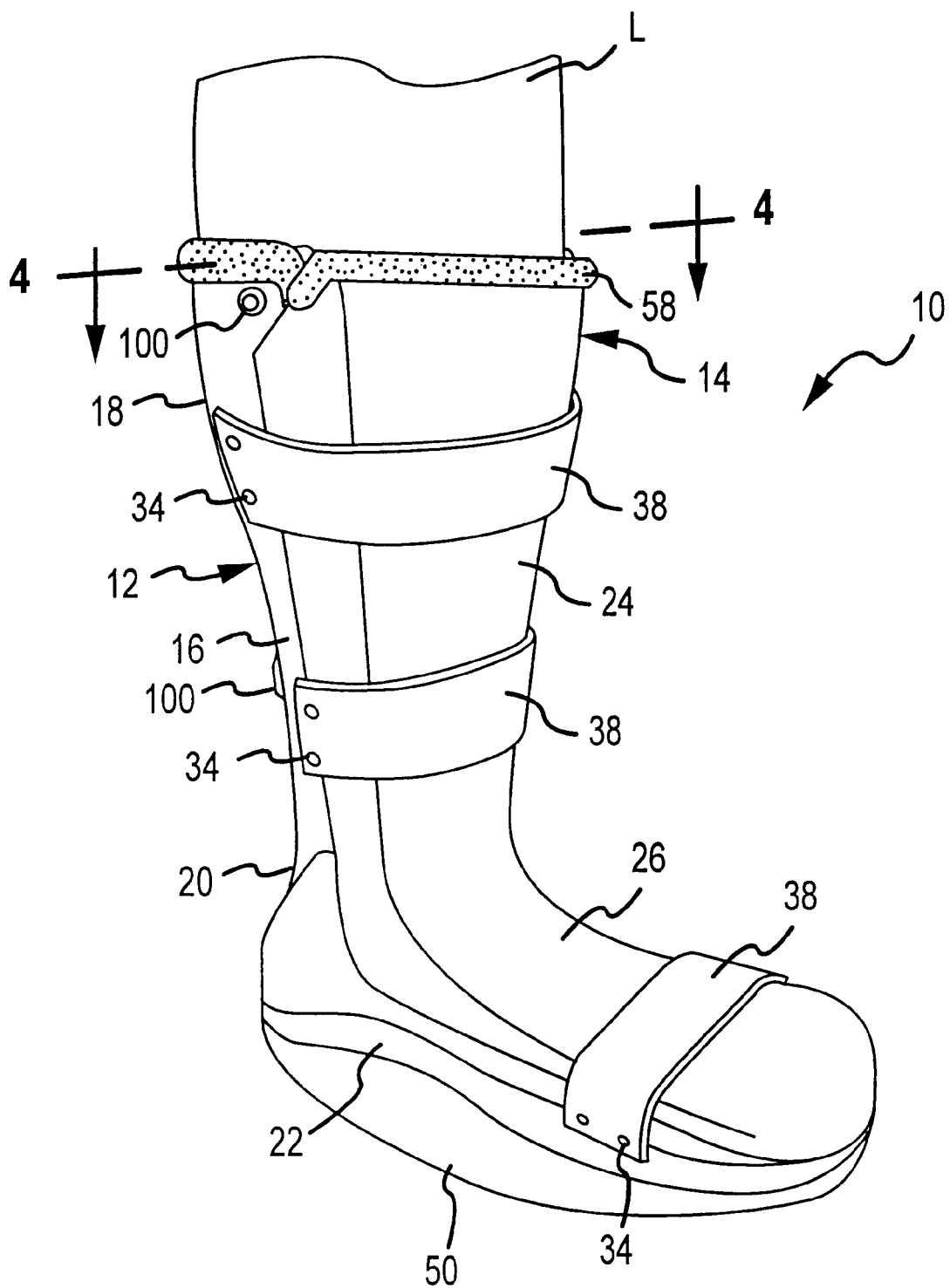
FIG. 1 is side view of a preferred embodiment of the brace of the present invention showing the brace assembled around the leg of a patient.
Figure 2:
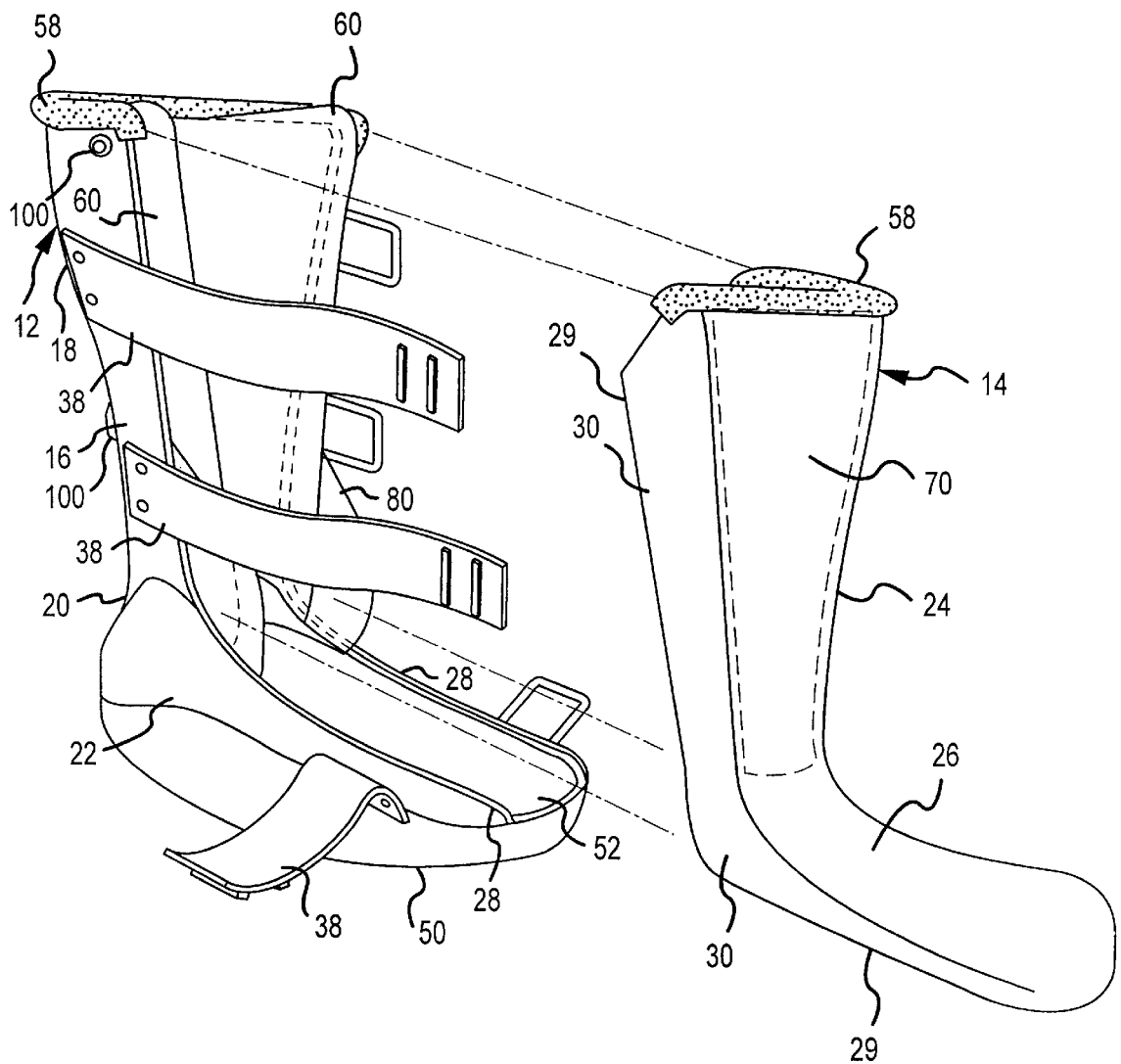
FIG. 2 is a side view of a preferred embodiment of the brace of the present invention in its disassembled configuration and without a patient's leg inserted therein.

As shown in FIGS. 1 and 2, the brace of the present invention is generally indicated as 10 and is specifically designed, as set forth in detail below, to effectively off-weight the plantar surface of a patient suffering from plantar sores and ulcerations while still allowing free and comfortable ambulatory motion for the patient wearing the brace. In short, a significant portion of the downward force is removed from the patient's plantar surface. The term "noff-weight" is defined herein to mean the transfer of a patient's weight from a plantar surface to the shells and adjustable bladders that comprise the brace of the present invention.

Hence, as noted above, the brace of the current invention differs significantly from the adjustable casts that are currently available. These casts are designed primarily to immobilize an area contiguous to the fracture to prevent the fractured limb from flexing. The device of the current invention, however, functions as a brace rather than a cast. In particular, the brace redistributes or redirects a patient's weight from the plantar surface to the brace itself. In so doing, the brace effectively off-weights the plantar surface. The brace of the present invention also significantly reduces shearing forces to the plantar surface and minimizes shearing forces at the plantar surface, thereby allowing the ulcerations to heal.

The general nature of a preferred embodiment of the instant invention may be readily understood with reference to FIGS. 1 and 2. The brace of present invention comprises a first rigid shell 12 and a second rigid shell 14 which are generally shaped to conform to the shape of the lower leg and foot. Thus, the shells 12, 14 have a generally semi-cylindrical cross-sectional configuration and are essentially in the shape of an "L." Each of the shells 12, 14 has two edges that run the entire length of the shell 28, 29.

The first shell 12 preferably includes a vertical section 16 which extends substantially from the patient's heel upwardly to a height equal to roughly the calf. The vertical section 16 includes a first section which is shaped to at least partially surround the calf 18 and a second section which is adapted to conform to the rear of the ankle and heel 20. The vertical section 16 preferably surrounds approximately three-quarters of the circumference of the leg. The first shell 12 also includes a lower horizontal section 22 which extends from the heel outwardly at substantially a right angle from the vertical section 16. The horizontal section 22 is adapted to at least partially surround the plantar surface and sides of the foot. The horizontal section 22 preferably extends horizontally a sufficient distance from the heel to surround at least a majority of the foot which is received therein and most preferably extends the entire length of the foot.

The second shell 14 has a similar configuration. The vertical section 24 of the second shell is adapted to receive the front of the lower leg or shin. A horizontal section 26 of the second shell extends outwardly at roughly a right angle from the vertical section 24 and is shaped to at least partially surround the instep and upper portion of the foot. Preferably, the horizontal section 26 of the second shell extends outwardly from the vertical section 24 a distance which covers at least a majority of the upper foot and most preferably extends to cover the entire length of the upper foot such that, together with the horizontal section 22 of the first shell, the entire foot is enclosed by the shells.

At least one bladder is disposed within the interior space of each of the first and second shells. The bladders are bags formed from plastic sheets which have been sealed along the outside edges. The bladders contain a filler. At least some of the bladders are adjustable and include an injection valve through which filler can be added or removed. Thus, the term adjustable refers to the fact that the size or volume of the bladder can be readily adjusted by either adding or removing filler from the bladder. This is a particularly important feature in that it allows the interior space of the brace to be varied in accordance with variations in the leg sizes of different patients as well as with changes in an individual patient's leg so as to maintain a constant pressure between the bladder and the leg. Preferably, the bladder placed within the first shell is adjustable, whereas the bladder in the second shell need not be adjustable.

Figure 4:
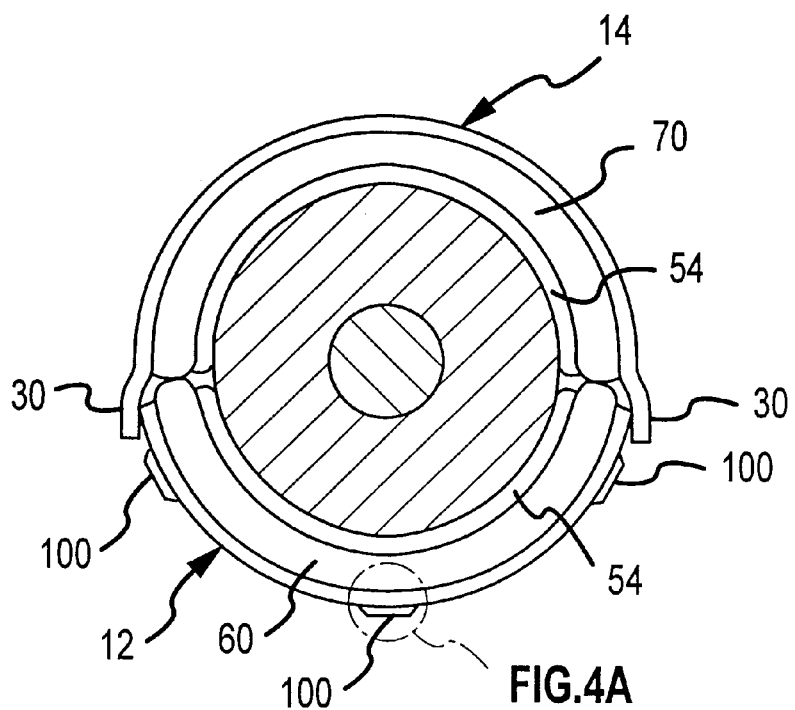
FIG. 4 is a cross-sectional view taken along 4—4 of FIG. 1 showing the relationship between the shells, bladders and absorption layers and further illustrating the way in which the flared edge of the second shell preferably slightly overlaps the longitudinal edge of the first shell.
Figure 5:
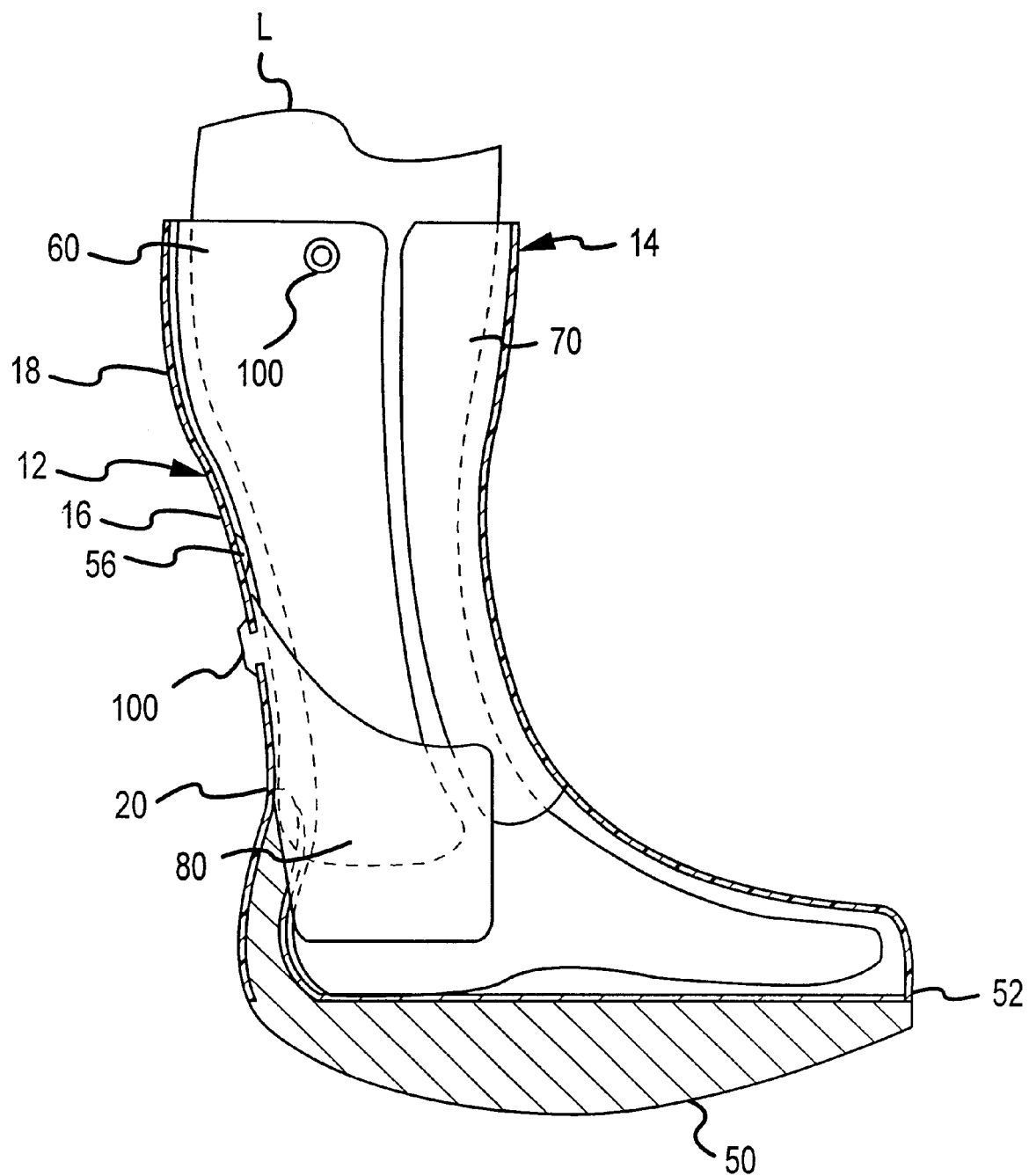
FIG. 5 a sectional view showing the positioning of the different bladders in a preferred embodiment of the brace.
Figure 7:
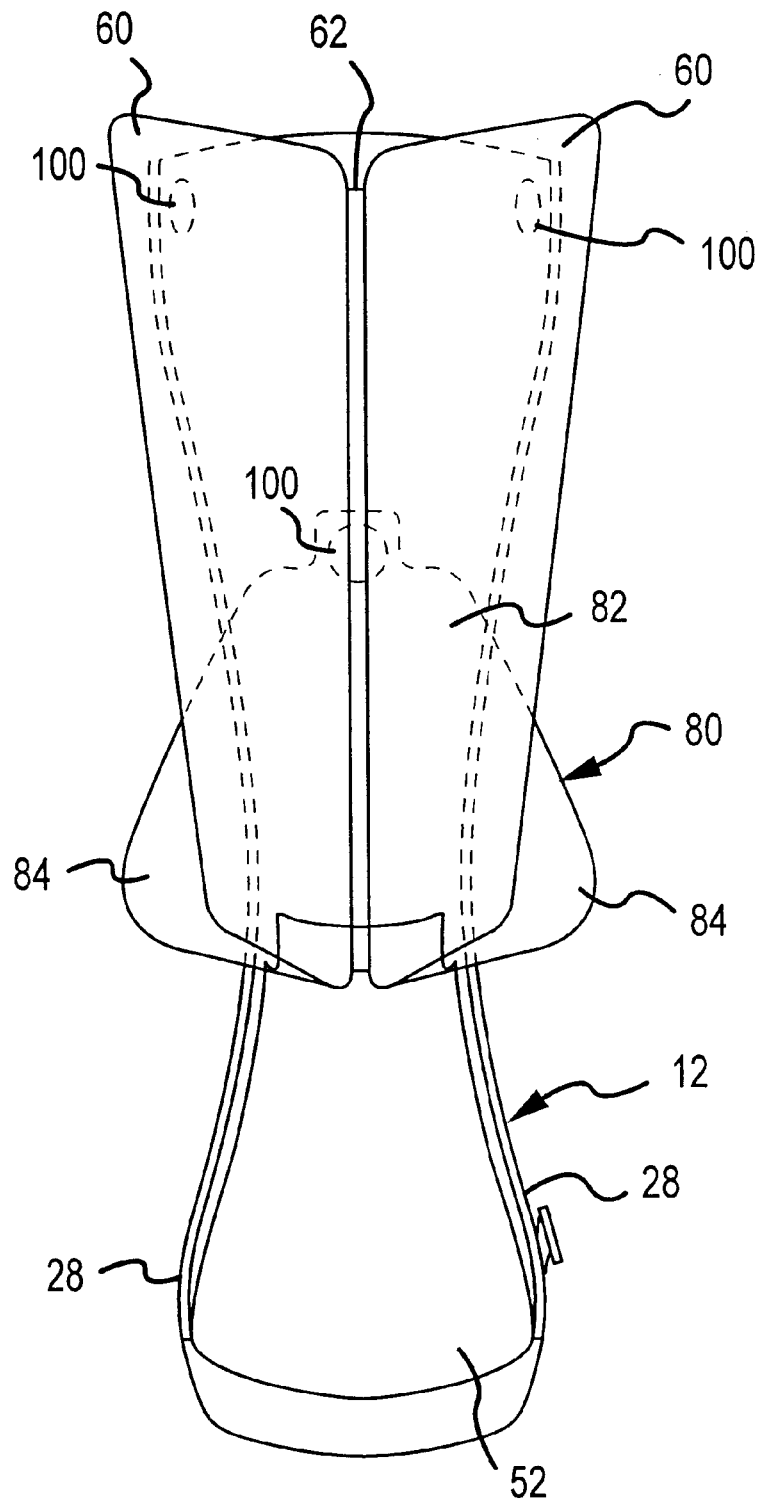
FIG. 7 is a front sectional view illustrating a preferred orientation of the first and third bladders within the first shell of the brace.
Figure 7A:
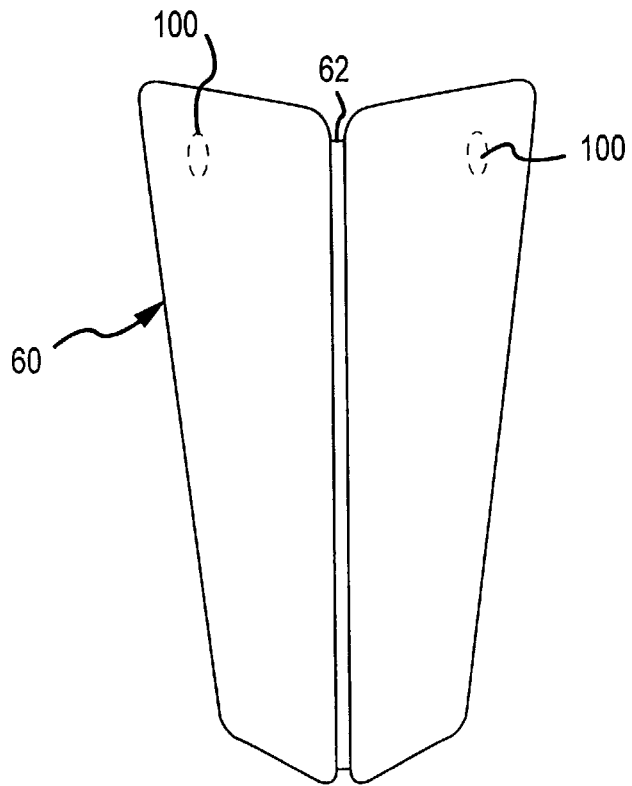
FIG. 7A illustrates a preferred general shape for the first bladder that is placed within the first shell of the brace.
Figure 7B:
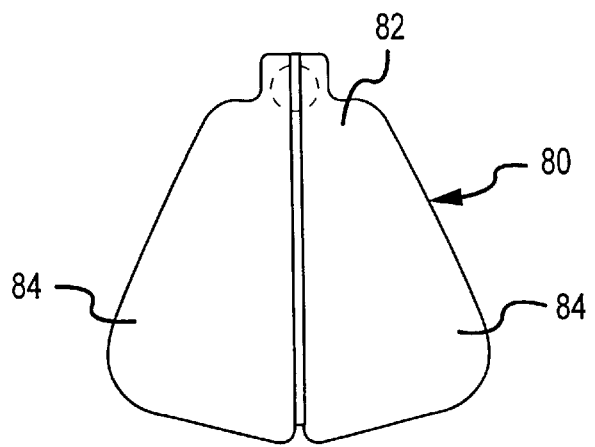
FIG. 7B depicts a preferred general shape for the third bladder than can be placed within the first shell of the brace.

As best seen in FIGS. 2, 4 and 5, the first shell 12 has concentrically disposed therein a first adjustable bladder 60 which generally conforms to the interior curvature of the shell but which may extend beyond the width of the shell on either side to surround a greater portion of both sides of the leg than the shell itself. The first bladder 60 typically extends essentially the entire length of the vertical section 16 of the first shell, thereby encompassing the calf and ankle regions of the leg, L. This first bladder 60 preferably is formed by a radiofrequency welding process such that a thin weld 62 extends vertically downward the length of the bladder, thereby dividing the bladder into two sections (see FIG. 7A). Each section preferably has an inlet valve 100 molded or welded into an upper portion of the bladder through which additional filler material can be added or removed in accordance with changes in leg size.

Referring again to FIG. 2, a second bladder 70 is concentrically disposed within the second shell 14 and generally conforms to the interior curvature of the second shell. Whereas the first bladder 60 may extend beyond the width of the first shell 12, the second bladder 70 generally covers the entire interior surface of the second shell 14 but does not extend beyond the longitudinal edges 29 thereof. Unlike the first bladder 60 placed in the first shell 12, the second bladder 70 typically is not divided into subsections and need not be adjustable. In those cases when the second bladder is not adjustable, the second bladder 70 is completely sealed and contains a fixed volume of a relatively noncompressible material and thus acts as a pillow or cushion for the front part of the leg. The combination of the first and second bladder 60, 70 preferably substantially surround the patient's leg.

Referring now to FIGS. 5–7B, in a particularly preferred embodiment a third adjustable bladder 80 is positioned within the first shell 12 and extends vertically from about the mid-heel area of the ankle region 20 approximately midway up the vertical section 16 of the first shell, i.e., to about mid-calf height. Preferably, this third bladder 80 has a central region 82 and wings 84 on either side thereof (see particularly FIG. 7B). Viewing the brace from the front as it stands vertically upright (FIG. 7), the central region of the third bladder 82 is centered within the interior portion of the first shell 12. The wings 84 of the third bladder when fully extended (prior to placing a leg within the shell) extend outwardly beyond both edges 28 of the first shell. Hence, once a foot is inserted into the first shell 12, the center part 82 of the third bladder 80 surrounds the Achilles heel region and the wings 84 of the third bladder can be wrapped at least partially around the sides of the patient's ankle. The third bladder 80 is also preferably positioned between the first shell 12 and the first bladder 60. This arrangement allows the inlet valve 100 welded onto the third bladder 80 to be conveniently extended through a lower portion of the first shell 12, thus allowing the facile addition or removal of filler material from this bladder (see FIG. 5). The welds in the first and third bladders 60, 80 are preferably positioned so that the welds of one bladder overlap with a non-welded region in the other bladder so as to avoid the creation of pressure points against the leg. As described in additional detail below, the third bladder 80 can act to securely immobilize the ankle within the brace, thereby preventing the foot from moving up and down relative to the footbed 52. This helps to eliminate contact between the footbed and the metatarsal region which is an area where foot ulcers are particularly prevalent.

Figure 6:
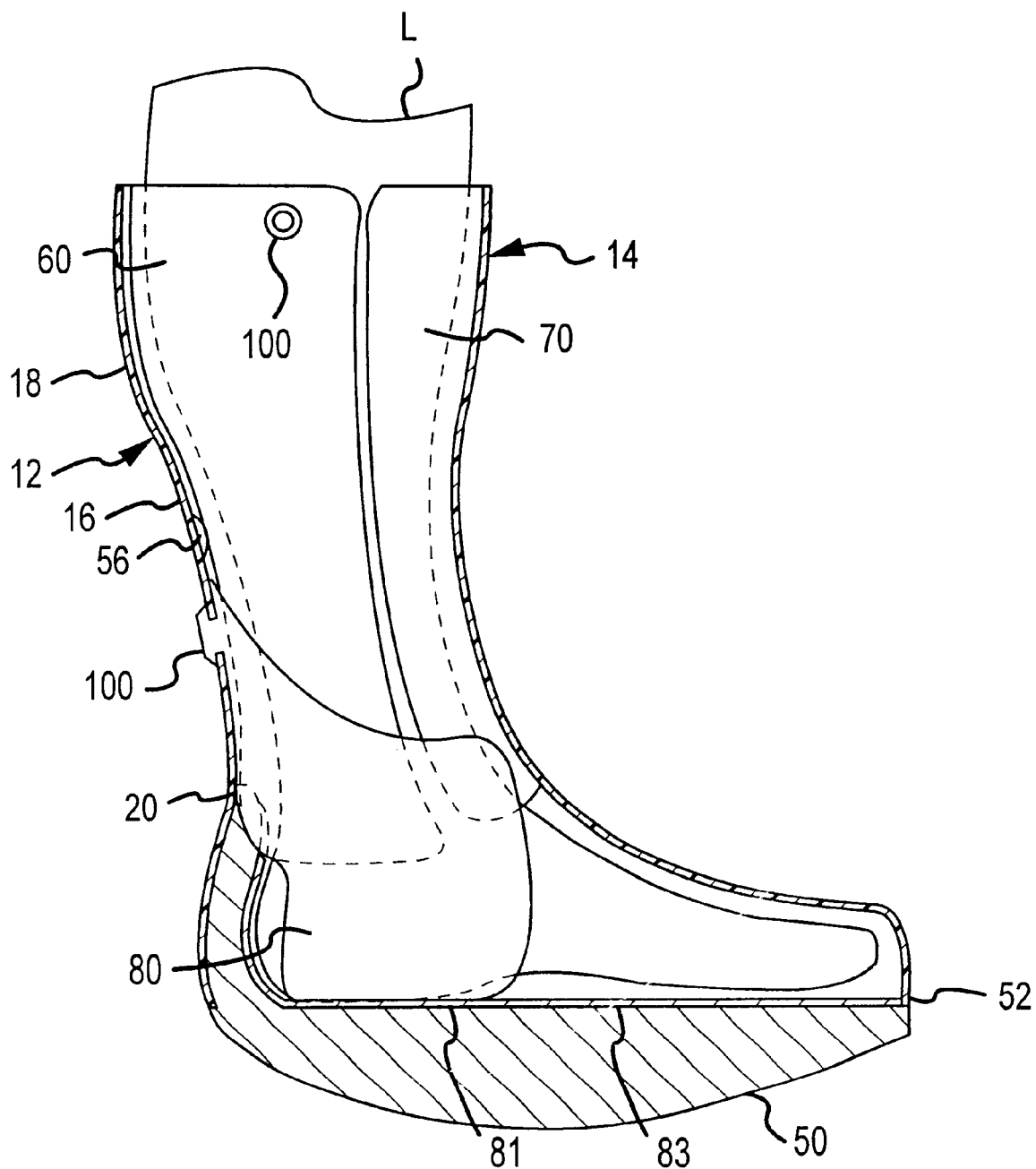
FIG. 6 is another sectional view showing the positioning of the different bladders in another preferred embodiment in which the third bladder is expanded to extend beneath the heel of the patient.

As illustrated in FIG. 6, in some instances it may be desirable to extend the third bladder 80 into the heel region 81 of the footbed 52 to elevate the heel to further reduce the likelihood of contact between the metatarsal region of the patient's foot and the footbed. The third bladder 80 can be extended even further yet to include the midfoot region 83 of the footbed to reduce further the possibility of contact.

The material used to fill the various adjustable bladders can vary. In general, the filler material selected should be one that undergoes only minimal expansion or contraction with changes in altitude or as the temperature within the brace fluctuates. This type of filler is important in avoiding pistoning of the leg within the brace. Such movement, of course, could result in the plantar surface making direct contact with the footbed, thereby further aggravating the ulcerations and delaying the time for healing. Examples of such fillers include non-compressible silicone, injectible polyurethane foam, silicone and wax liquid composites and compressible silicone liquid. The use of noncompressible silicone has been shown to give particularly good results and to effectively negate pistoning of the leg in the brace even with the temperature changes which commonly occur within a patient's brace.

Existing adjustable casts are designed primarily for fracture care and have typically utilized inflatable bladders that are filled with air. Use of air inflated bladders for the treatment of plantar ulcerations, however, is not preferred, because of the tendency for air to expand or contract with temperature fluctuations within the brace. The fillers listed above all expand and contract less in response to temperature and altitude changes than air. Expansion can create painful pressure against the leg and can aggravate the circulation problem diabetic patients already experience. Contraction of the filler material, as just noted, results in harmful pistoning of the leg within the brace.

Figure 4A:
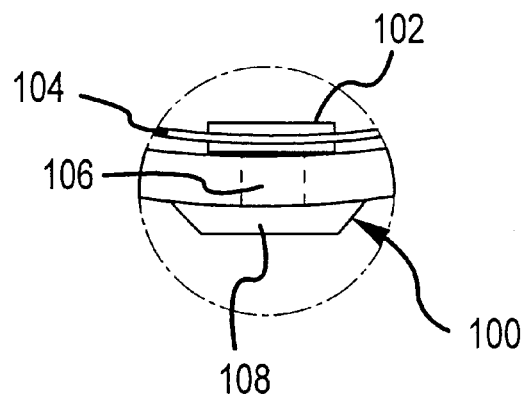
FIG. 4A is an enlarged view of an inlet valve as depicted in FIG. 4.

The inlet valve 100 through which filler is added or removed is preferably made of a tubular piece of plastic that has two ends. As shown in FIG. 4A, one end 102 is molded or welded into one of the bladder sheets 104. The end of the injection port which is not connected to the bladder preferably includes a flexible cap 108. The inlet valve 100 extends through an aperture 106 in the shell to facilitate the addition or removal of material from the exterior of the brace. The cap 108 is sufficiently flexible so that it can be forced through the aperture 106 in the shell. However, the cap 108 is larger than the aperture 106 so that once the cap has been forced through the aperture it expands along the exterior of the brace and assists in holding the bladder in the proper location. However, the inlet valve can be made of alternate materials, have a different structure and be located at other positions as would be appreciated by those skilled in the art.

Figure 9:
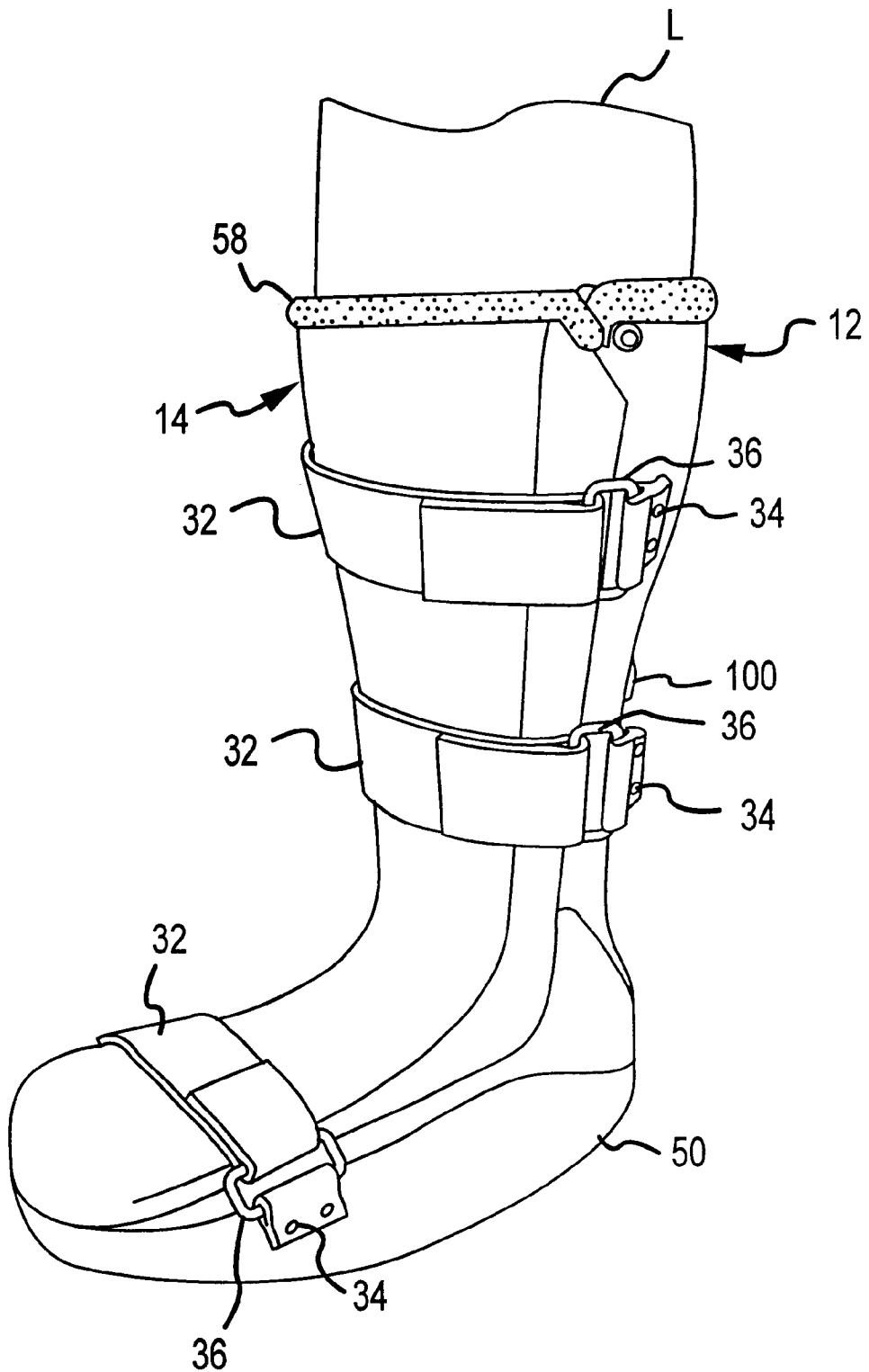
FIG. 9 is a side view of another embodiment of the brace depicting a fastening system that comprises a plurality of belts made of hook-and-pile material that can be used to connect the brace shells together.

The two shells of the brace 12, 14 are joined by first placing the shells in abutting relationship with respect to one another. The second shell 14 preferably has flared longitudinal edges 30 as indicated in FIGS. 2 and 4 so that the flared edges of the second shell slightly overlap those of the first shell 12. The two shells 12, 14 are then fixedly connected or immobilized with respect to one another by the use of a fastening system. The fastening system can include belts manufactured of a hoop and pile material (most commonly sold under the trademark VELCRO). With reference to FIGS. 1 and 9, one possible arrangement includes a plurality of belts 32 each of which contain separate sections of both hoop and pile material. One end of the belt 32 is connected by rivets 34 to one exterior side of the first shell 12; a metal loop 36 is attached by anchor rivets 34 to the opposite exterior side of the first shell. The belt 32 is then extended over the second shell 14, passed through the metal loop 36 and returned back over the second shell. The hook and pile sections of the belt 32 which overlap are then connected to create a secure attachment between the two shells 12, 14.

Figure 8:
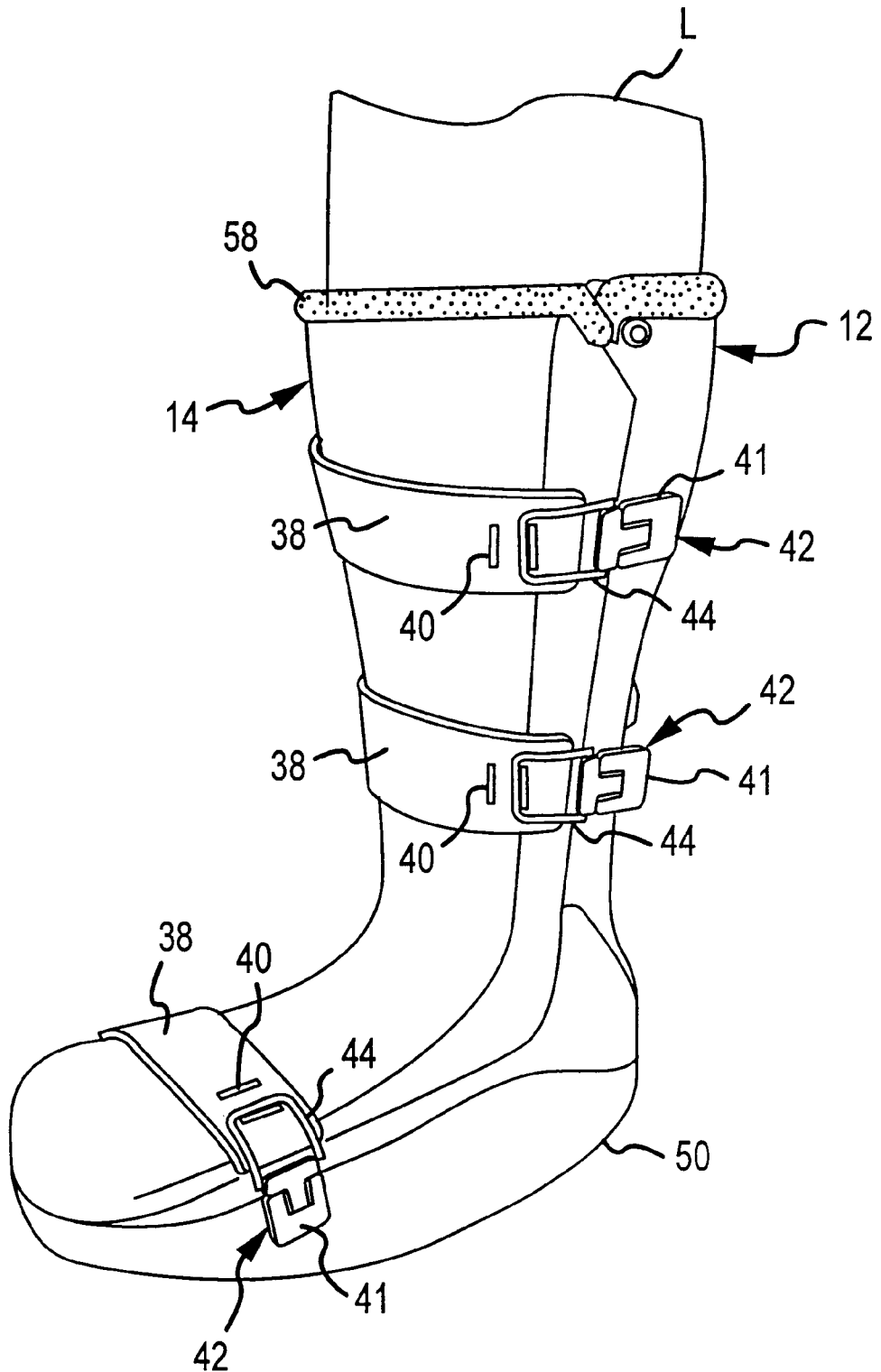
FIG. 8 is a side view of a preferred embodiment of the brace showing a fastening system comprising a series of straps having a plurality of ridges and a cam-type buckle system having a hook for attaching to the ridges.

A more preferred fastening system is illustrated in FIG. 8 and includes a plurality of straps 38 and a cam-type buckle unit 42. The strap 38 is connected by rivets 34 to one side of the exterior of the first shell 12 and contains a plurality of ridges 40, but preferably contains only two ridges. The cam-type buckle unit 42 is attached on the exterior of the opposing side of the first shell. The cam-type buckle unit 42 includes a hoop 44 that can engage the ridge 40 on strap 38. When a lever 41 of the cam-type buckle unit 42 is pushed into the closed position, the strap 38 is held securely in place. A variety of other fastening systems could also be used provided the system securely holds the two shells together to form a unified brace structure.

As shown in FIGS. 8 and 9, the fastening system preferably includes three straps or belts. Two straps or belts are positioned on the vertical section of the first shell. In general, one strap or belt is positioned near the top of the vertical section and another strap or belt is positioned near the mid-point of the vertical section of the first shell, i.e., about mid-calf level. The third strap or belt is preferably located at approximately the instep of the foot.

The fastening system preferably also includes a locking means which prevents the patient or unauthorized personnel from opening the brace; alternatively, the locking means may be designed so that the patient can unlock the fastening system but not without the unlocking being obvious to the attending physician. Examples of potential systems include a pin and hole system or a wire and clamp system. In these cases, the pin cannot be removed or the wire cannot be cut without such action being obvious to the physician. This is an important feature of the brace design to ensure patient compliance with the treatment regime prescribed by the attending physician.

A sole walker or rocker 50 is attached to the underside of the horizontal section 22 of the first shell as shown in FIGS. 1 and 2. The sole walker 50 can be made of a variety of non-slip materials. Examples of such materials include crape rubber, hard rubber, a VIBRAM sole or other alternative rubber based materials. The sole walker 50 can also have a tread design molded therein to further reduce the likelihood of a patient slipping while walking with the brace. The sole walker 50 preferably extends essentially the entire distance of underside of the horizontal section 22 of the first shell. In a preferred embodiment, the sole walker 50 has convex curvature as shown in FIG. 5. The current inventors have found that sole walkers 50 that are curved, particularly those in which the rockers have a greater radius in-line with the patient's tibia, result in the patient spending more time on the heel and less time on the forefoot. This design helps eliminate the propulsive phase of gait and is important in minimizing the shearing forces on the metatarsal region where ulcers are more prevalent.

This particular combination of elements yields a brace which is effective in treating plantar ulcers, including those on the feet of patients suffering from neuropathy. In particular, the adjustable bladder(s) in combination with the cushioned bladder located in the second shell provide a uniform pressure around the entire leg and ankle region. This uniform pressure means that a patient's weight can be effectively transferred from the plantar surface and redistributed to the shells of the brace, thereby eliminating or significantly reducing the direct downward pressure or force exerted on the plantar surface, especially the metatarsal region which is particularly susceptible to plantar ulcerations.

Furthermore, the combination of the wings of the third bladder 84 which wrap alongside the side of the ankle and the additional support provided from the first bladder are important features in preventing the foot from plantar flexing (i.e., preventing the foot from flexing at the ankle, thereby keeping the foot in a primarily horizontal orientation during ambulation). For patients suffering from plantar foot ulcerations, the fact that the first and third bladders cooperate to effectively restrict foot motion is particularly critical, as this keeps the foot from flexing downward and contacting the footbed located in the first shell. If the foot were allowed to plantar flex, the shearing forces generated as the plantar surface rubbed against the footbed would further aggravate any sores or ulcerations and hinder the healing process. Thus, unlike the casts developed to date, the positioning of adjustable bladders in the brace of the current invention effectively prevent plantar flexing, off-weight the foot and reduce shearing forces to the plantar surface—a combination of results which is required for effective treatment and timely healing of plantar ulcerations. These combination of results make the cast especially beneficial in treating plantar ulcers for patient's suffering from diabetic neuropathy. This contrasts with certain existing air inflatable casts which contain warnings that the casts should not be used by patients incapable of communicating physical discomfort.

Figure 3:
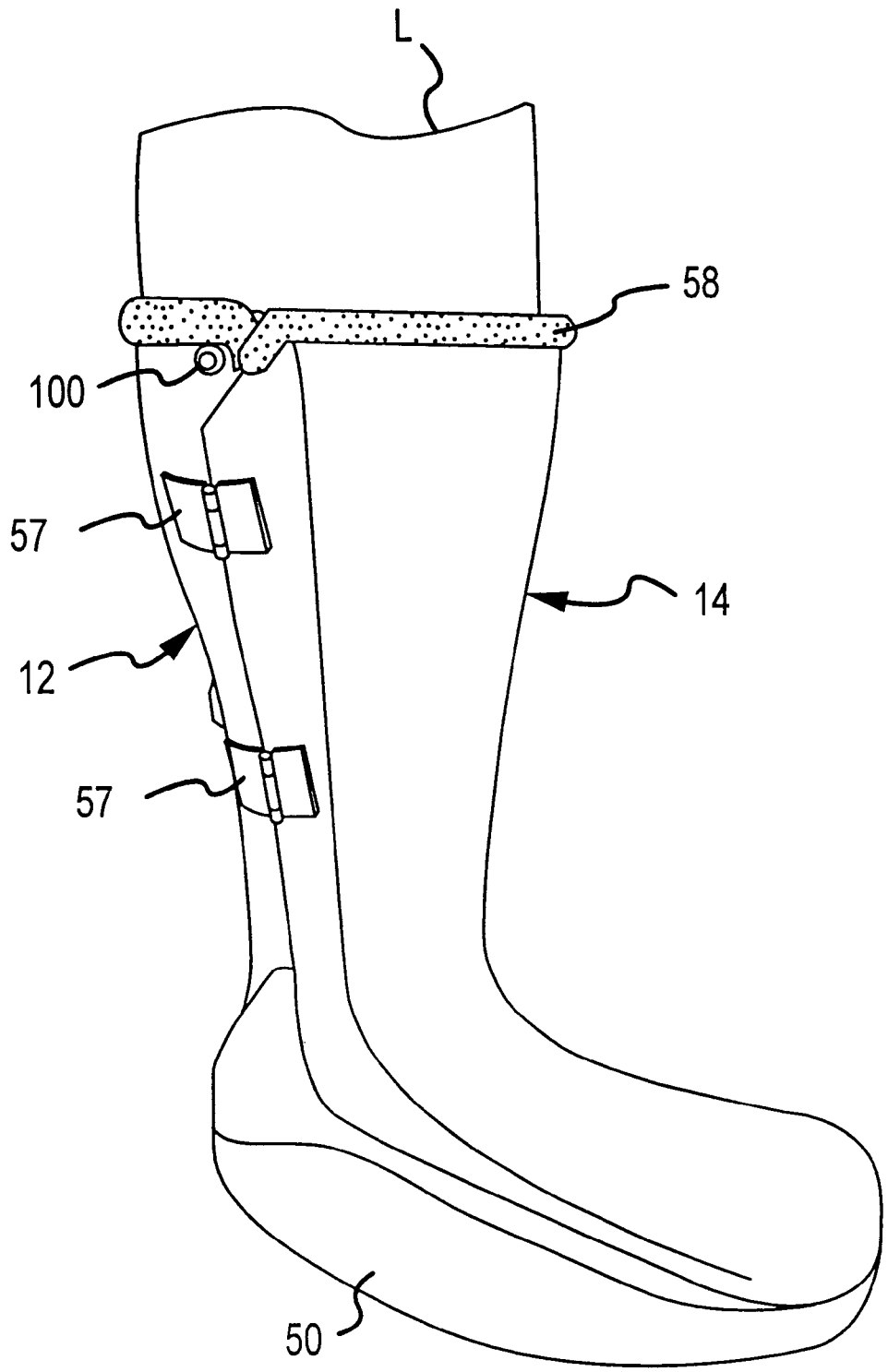
FIG. 3 is a side view of the brace of the present invention showing the location of optional hinges on the brace.

Variations of this general design can be utilized to further enhance the effectiveness, convenience and comfort of the brace. For instance, preferably, the inner diameter of the first and second shell members are tapered inward near the ankle region and tapered outward near the upper leg region to more closely match the physical dimensions of an average human leg. If desired, hinges 57 such as those shown in FIG. 3 may also be attached near the edges of the first and second shells 12, 14 to facilitate the joining of the two shells once a patient's leg has been placed between the shells. In order to enhance patient comfort, a narrow foam cuff 58 is preferably adhered to the upper edges of the vertical sections of the first and second shell which are in contact with the calf and shin, respectively (see FIGS. 1 and 2).

Although the volume of the adjustable bladders can be varied to accommodate a variety of leg sizes as described above, the effectiveness of the brace can be optimized by the use of various sized braces. Typically, three sizes—small, medium and large—are sufficient to accommodate nearly all patient leg sizes. In fact, braces according to the present design have been effectively used to treat patients in which the smallest part of the calf size ranged from 19 to 26 inches in circumference and in which the largest part of the calf ranged from 23.5 to 49.5 inches in circumference.

A variety of plastic materials can be utilized in the construction of the brace, provided the materials establish a rigid shell structure. Polypropylene and rigid polyurethane are examples of preferred plastic materials. The thickness of the shells is preferably between 0.125 and 0.156 inches thick and most preferably is 0.156 inches thick. The desired shape and taper can be achieved using standard thermoforming processes.

The material selected for the interior of the horizontal section of the first shell, i.e., the footbed 52 (see FIGS. 2 and 7), should have minimal resistance to shearing forces. Examples of materials satisfying this criterion include silicone, low density foam materials such as polyolefin-based compressible foam, polyurethane foam rubber and open-cell polyurethane and polyethylene in the 1.5 lb to 3.0 lb per cubic foot density range. The material making up the footbed 52 generally is cut to cover the entire width and sides of the horizontal section of the first shell as illustrated in FIG. 2. The material can be die cut or thermoformed to the proper size and shape. Adhesive or double-backed adhesive tape can be used to securely fasten the material to the footbed.

Typically, the bladders are manufactured of a urethane material, although other plastic materials could also be utilized. Such materials, however, do not allow body heat generated between the leg and the bladder to easily escape. Hence, as illustrated in FIG. 4, an absorbent layer 54 is preferably attached to the surfaces of the bladders which abut the surface of the leg. This arrangement places an absorbent layer 54 which can absorb perspiration between the bladder and the leg surface. The absorbent cloth can also reduce the incidence of allergic reactions to the bladder material. Examples of materials that can be used for the absorbent layer include, but are not limited to, felt cloth and cotton materials.

Pressure transducers or sensors 56 can also be sandwiched between a shell wall and a bladder to monitor the pressure of the bladders against the patient's legs (see FIGS. 5 and 6). This is important in ensuring that a constant pressure is maintained throughout the treatment period and to protect against unduly high pressures which might cause discomfort to the patient and hinder circulation through the leg. Alternatively, pressure at the leg can be determined from the back pressure at the inlet valve using known correlations between back pressure at the valve and pressure at the leg.

With this description of the brace itself, the method of using the brace of the present invention to treat patient's having plantar ulcerations can be readily understood, particularly with reference to FIG. 2. The two shells 12, 14 are initially separated. If hinges are used to join the shells 12, 14, than one of the shells is swung open to provide access to the interior regions of the shells. The patient's leg, L, is then positioned within the first shell 12 and the first bladder 60 positioned to surround the calf region 18 and Achilles' heel region 20 of the patient. If the third bladder 80 is used, it is also arranged in the ankle region and the opposing wings can be positioned alongside the sides of the patient's ankle. The second shell 14 including the second bladder 70 is then placed over the shin and top of the patient's foot to enclose the patient's leg, being carefull to ensure that the various bladders essentially completely surround the patient's leg (as shown in FIG. 4). In joining the second shell 14, the flared edges 30 of the second shell are placed over the edges of the first shell 28. The two shells 12, 14 are then fixedly joined using the straps or belts 38 attached to the first shell, after first passing the straps or belts over the second shell, to form a unified brace. A locking means connected to the fastening system can be employed to keep the patient from removing the brace, thereby assuring patient compliance with the physician's treatment instructions. Of course, the order in which the shells are applied to the leg could be reversed.

The desired pressure in the shells is achieved by injecting the appropriate amount of filler into the adjustable bladders. As noted above, a preferred filler is non-compressible silicon, although injectible polyurethane foam, silicone and liquid wax composites, and compressible silicone liquid can also be used. The filler material can be injected into the adjustable bladders through the injection ports welded into each bladder using a device which is very similar to a caulking gun. A hand trigger is used to pump the silicone out of silicone tubes that are typically 6 to 8 inches in length. Preferably, the inlet valve contains an internal valve which is opened when the nozzle of the gun is inserted therein and then closes when the nozzle is withdrawn. The filler could also be injected by various manual or automatic pumping systems. As noted earlier, the desired pressure can be monitored using sensors located between the interior shell wall and the adjustable bladder or from correlations between back pressure at the inlet valve and pressures on the leg. The volume of filler in the bladders is adjusted to provide the uniform pressure necessary to ensure that the plantar surface of the patient's foot is effectively off-weighted and plantar flexing minimized.

As the volume of the patient's leg changes due to edema or atrophy, proper pressure can be restored by adding or withdrawing filler as appropriate. Since the bladders are adjustable, they can also be reused simply by adding or withdrawing filler as necessary.

While the present invention has been described with respect to several preferred embodiments, and while changes and modifications have been discussed, it should be understood that various other changes and modifications could be made to the brace of the present invention without departing from the broad scope of the current invention. For example, other fillers besides those listed herein could be used so long as the fillers satisfy the general requirement of expanding or contracting less than air in response to temperature or altitude changes. The type of fastening system could also vary from the VELCRO and buckle and cam systems described herein. Similarly, a number of different locking schemes could be utilized.

We claim:

1. A method for treating ulcerations on a plantar surface of a patient's foot, comprising:
    (a) inserting a patient's leg between a first and second rigid shell, said first and second shell being generally L-shaped, having a generally semi-cylindrical cross-sectional configuration and being adapted for receiving a lower leg and foot of said patient;
    (b) positioning a first adjustable bladder so that said adjustable bladder is sandwiched between said first shell and said leg; wherein said positioning step involves arranging said first adjustable bladder between said first shell and said leg and arranging a non-adjustable bladder between said second shell and said leg;
    (c) fastening said first and second shell together using a fastening system to form a unified brace; and
    (d) adjusting the volume of said first adjustable bladder to engage said brace against said leg such that said plantar surface is off-weighted and shearing forces at said plantar surface and plantar flexing are significantly reduced.

2. A method for treating ulcerations on a plantar surface of a patient's foot, comprising:
    (a) positioning said patient's leg in a first shell, said first shell being generally shaped and having a vertical and horizontal section adapted to receive a lower leg and foot of said patient;
    said vertical section of said first shell having sufficient longitudinal dimension to extend from a calf of said leg to a location beneath a heel potion of said foot, thus including a calf section and an ankle section which are adapted to receive said calf and an ankle of said patient, respectively, and said horizontal section of said first shell extending outwardly from said vertical section of said first shell and having sufficient length to receive at least a majority of said foot;

(b) placing over the front of said individual's leg a second shell, said second shell being generally L-shaped and having a vertical and horizontal section and being adapted to cover said lower leg and said foot; said vertical section of said second shell having sufficient longitudinal dimension to extend from a shin of said leg to an instep of said leg, and said horizontal section of said second shell extending outwardly from said vertical section of said second shell and having sufficient length to cover a majority of said foot;

(c) fastening said first and second shells using a fastening system to form a unified brace; and (d) adjusting the volume of at least one of a first and second bladder to create a desired pressure against said leg and to engage said brace against said leg such that said leg is essentially immobile within said brace and said plantar surface is off-weighted; said at least one of a first and second bladder being disposed in said first and second shell, respectively, and said at least one of said first and second bladder containing a filler which undergoes minimal expansion and contraction as the temperature in said brace fluctuates so that said desired pressure against said leg is maintained to allow said ulcerations to heal.

3. The method of claim 2, wherein said filler is selected from the group consisting of non-compressible silicone, injectible polyurethane foam, silicone and wax liquid composites, and compressible silicone liquid.

4. The method of claim 2, further including a third bladder, said third bladder being generally positioned in said ankle section of said first shell.

5. The method of claim 2, wherein the volume of said first and third bladder is adjustable.

6. The method of claim 2, wherein said first bladder extends substantially the length of said vertical section of said first shell and said second bladder extends substantially the length of said vertical section of said second shell.

7. The method of claim 2, wherein said third bladder is sized to at least partially wrap around said ankle.

8. The method of claim 2, wherein said third bladder includes a central section which is adapted to be connected to said first shell and a first wing and a second wing on opposing sides of said central section, said first and second wing being sized to at least partially wrap around the sides of said ankle.

9. The method of claim 2, wherein the volume of said first bladder is adjustable and wherein the volume of said second bladder remains essentially constant.

10. The method of claim 2 further including a step of engaging a locking means, said locking means restricting the ability of said patient to operate said fastening system.

11. The method of claim 2, wherein:

(a) said first bladder extends substantially the length of said vertical section of said first shell and said second bladder extends substantially the length of said vertical section of said second shell;

(b) said third bladder is sized to at least partially wrap around said ankle;

(c) the volume of said first and third bladder is adjustable; and (d) said first, second and third bladder contain said filler, said filler being selected from the group consisting of non-compressible silicone, injectible polyurethane foam, silicone and wax liquid composites and compressible silicone liquid.

12. A method for treating ulcerations on a plantar surface of a patient's foot, comprising:

(a) inserting the patient's leg between a first and second rigid shell, said first and second rigid shell being adapted for receiving a lower leg and a foot of the patient;

(b) positioning a first adjustable bladder so that said first adjustable bladder is sandwiched between said first shell and said leg;

(c) positioning a second bladder so that said second bladder is sandwiched between said second shell and said leg;

(d) fastening said first and second shell together using a fastening system to form a unified brace; and (e) adjusting the volume of said first adjustable bladder by adding or removing a substantially incompressible filler to off-weight the patient's foot to allow said ulcerations to heal.

13. The method of claim 12, wherein said adjusting stop utilizes a filler that undergoes minimal expansion and contraction as the temperature in said brace fluctuates.

14. The method of claim 12, wherein said adjusting step utilizes a filler selected from the group consisting of non-compressible silicon, indictible polyurethane foam, silicone and wax liquid composites, and compressible silicone liquid.

15. A method for treating ulcerations on a plantar surface of a patient's foot, comprising:

(a) inserting the patients' leg between a first and second rigid shell, said first and second rigid shell being adapted for receiving a lower leg and a foot of the patient;

(b) positioning a first adjustable bladder so that said first adjustable bladder is sandwiched between said first shell and said leg;

(c) positioning a second bladder so that said second bladder is sandwiched between said second shell and said leg;

(d) fastening said first and second shell together using a fastening system to form a unified brace; and (e) adjusting the volume of said first adjustable bladder by adding or removing a substantially incompressible filler to elevate at least a portion of the patient's foot from an interior bottom surface of said brace to allow said ulcerations to heal.

* * * * *

UNITED STATES PATENT AND TRADEMARK OFFICE
CERTIFICATE OF CORRECTION

| | |
|---|---|
| PATENT NO. | : 6,228,044 B1 |
| DATED | : May 8, 2001 |
| INVENTOR(S) | : Jensen et al. |

It is certified that error appears in the above-identified patent and that said Letters Patent is hereby corrected as shown below:

Column 1,
Line 5, insert the sentence:

This invention was made with government support under 5 R44 DK 52745-03 awarded by the National Institute of Diabetes and Digestive and Kidney Diseases. The government has certain rights in the invention.

Signed and Sealed this

Thirtieth Day of April, 2002

*Attest:*

JAMES E. ROGAN
*Director of the United States Patent and Trademark Office*

*Attesting Officer*